(12) United States Patent
Liu et al.

(10) Patent No.: US 10,470,673 B2
(45) Date of Patent: Nov. 12, 2019

(54) HEADPHONE WITH BIOLOGICAL FEATURE DETECTION FUNCTION, INTERACTION SYSTEM AND BIOLOGICAL FEATURE DETECTION METHOD

(71) Applicant: SHENZHEN GOODIX TECHNOLOGY CO., LTD., Shenzhen OT (CN)

(72) Inventors: Chang Liu, Shenzhen (CN); Haixiang Wang, Shenzhen (CN); Hexing Liu, Shenzhen (CN); Lei Zhao, Shenzhen (CN)

(73) Assignee: SHENZHEN GOODIX TECHNOLOGY CO., LTD., Shenzhen (CN)

( * ) Notice: Subject to any disclaimer, the term of this patent is extended or adjusted under 35 U.S.C. 154(b) by 107 days.

(21) Appl. No.: 15/636,640

(22) Filed: Jun. 29, 2017

(65) Prior Publication Data

US 2017/0296077 A1 Oct. 19, 2017

Related U.S. Application Data

(63) Continuation of application No. PCT/CN2016/090611, filed on Jul. 20, 2016.

(30) Foreign Application Priority Data

Jan. 5, 2016 (CN) .......................... 2016 1 0005702

(51) Int. Cl.
*H04R 5/033* (2006.01)
*A61B 5/024* (2006.01)
(Continued)

(52) U.S. Cl.
CPC .......... *A61B 5/02438* (2013.01); *A61B 5/024* (2013.01); *A61B 5/02416* (2013.01);
(Continued)

(58) Field of Classification Search
CPC .. H04R 5/033; H04R 5/0335; H04R 2420/09; A61B 5/6803
See application file for complete search history.

(56) References Cited

U.S. PATENT DOCUMENTS

| 8,498,428 | B2* | 7/2013 | Schreuder | .............. | H04R 5/033 |
| | | | | | 381/74 |
| 8,755,782 | B2* | 6/2014 | Lim | .................. | H04M 1/72569 |
| | | | | | 340/1.1 |

(Continued)

FOREIGN PATENT DOCUMENTS

| CN | 102006528 A | 4/2011 |
| CN | 102065350 A | 5/2011 |

(Continued)

*Primary Examiner* — Curtis A Kuntz
*Assistant Examiner* — Ryan Robinson

(57) ABSTRACT

Embodiments of the present application provide a headphone with a biological feature detection function, an interaction system and a biological feature detection method. The headphone includes: a loudspeaker, a microphone, a biological feature detection module, a mode switching module, a first communication module, a control module and a power management module. The control module is configured to detect and determine whether an instruction is received from the smart terminal, and control, according to the instruction received from the smart terminal, the biological feature detection module, the mode switching module, the power management module and the first communication module to work, and further configured to parse the biological feature from the biological feature detection module under control of the instruction received from the smart terminal, and transmit the parsed biological feature to the smart terminal via the first communication module.

19 Claims, 5 Drawing Sheets

(51) Int. Cl.
*G16H 40/63* (2018.01)
*H04R 1/10* (2006.01)
*A61B 5/00* (2006.01)
*H04M 19/04* (2006.01)
*G10L 21/0208* (2013.01)

(52) U.S. Cl.
CPC ........... *A61B 5/6898* (2013.01); *G16H 40/63* (2018.01); *H04M 19/04* (2013.01); *H04R 1/1041* (2013.01); *H04R 1/1091* (2013.01); *G10L 21/0208* (2013.01); *H04R 2420/07* (2013.01)

(56) References Cited

U.S. PATENT DOCUMENTS

| | | | |
|---|---|---|---|
| 9,532,748 B2* | 1/2017 | Denison | A61B 5/04012 |
| 10,212,399 B2* | 2/2019 | Kim | G08B 21/02 |
| 10,258,243 B2* | 4/2019 | LeBoeuf | A61B 5/0205 |
| 2001/0046304 A1 | 11/2001 | Rast | |
| 2004/0209569 A1 | 10/2004 | Heinonen et al. | |
| 2006/0102171 A1 | 5/2006 | Gavish | |
| 2012/0156933 A1* | 6/2012 | Kreger | A61B 5/02433 |
| | | | 439/625 |
| 2015/0257662 A1 | 9/2015 | Lee et al. | |
| 2015/0312669 A1* | 10/2015 | Song | A61B 5/02438 |
| | | | 381/74 |
| 2019/0098395 A1* | 3/2019 | Keeling | G10K 11/17823 |

FOREIGN PATENT DOCUMENTS

| | | |
|---|---|---|
| CN | 102088511 A | 6/2011 |
| CN | 103873974 A | 6/2014 |
| CN | 104202691 A | 12/2014 |
| CN | 104244125 A | 12/2014 |
| CN | 104581472 A | 4/2015 |
| CN | 104581535 A | 4/2015 |
| CN | 104718766 A | 6/2015 |
| CN | 104754470 A | 7/2015 |
| CN | 104822103 A | 8/2015 |
| CN | 105100994 A | 11/2015 |
| CN | 105451115 A | 3/2016 |
| KR | 20130028570 A | 3/2013 |
| WO | 2014057921 A1 | 4/2014 |

* cited by examiner

HEADPHONE WITH BIOLOGICAL FEATURE DETECTION FUNCTION, INTERACTION SYSTEM AND BIOLOGICAL FEATURE DETECTION METHOD

This application is a continuation of international application No. PCT/CN2016/090611, filed on Jul. 20, 2016, which claims priority to Chinese Patent Application No. 201610005702.8, filed before Chinese Patent Office on Jan. 5, 2016, both of which are incorporated herein by reference in their entities.

TECHNICAL FIELD

Embodiments of the present application relate to the technical field of wearable devices, and in particular, relates to a headphone with a biological feature detection function, an interaction system and a biological feature detection method.

BACKGROUND

Headphones are an entertainment tool frequently used by people, and are small in size and convenient to wear. Therefore, the headphones are widely used in people's life and work. For example, people may listen to music via the headphones while they are doing morning exercise, and may wear the headphones to watch videos, enjoy music and practice their English listening when they are going to work or going home after work.

However, with the development and advancement of science and technology, the function of the headphone is not limited to the single function of a traditional headphone. Smart headphones are being used among people. For example, smart headphones capable of detecting heart rate information of human bodies by detecting vibration at the auricle are well populated. Currently, a variety of headphones capable of detecting biological feature information of human bodies are welcome. The biological features may be categorized into physiological features (for example, fingerprint, face image, iris, palm print and the like) and behavior features (for example, gait, voice, handwriting and the like). The biological feature detection signifies identification and identity authentication of an individual based on the unique biological features of the individual.

At present, headphones capable of detecting the heat rate information of human bodies are available in the prior art. However, such information detection is practiced by using an external mechanical key on a headphone. That is, in such headphones, users' manual operations on external the mechanical key on the headphones are needed, such that the headphones are manually switchable between a voice call mode and a heart rate detection mode. For example, when a user holds too many articles on his or her hands, such headphones are not convenient to use. Therefore, the headphones in the prior art need users' manual operations on the mechanical keys on the headphones to implement the biological feature detection function. As a result, convenience of users' operation, application scope and user experience are all affected.

SUMMARY

In view of the above defect of the headphone for implementing biological feature detection in the prior art, embodiments of the present application provide a headphone with a biological feature detection function, which is capable of completely automatically implementing the biological feature detection function.

To solve the above technical problem, the embodiments of the present application provides a headphone with a biological feature detection function, including: a loudspeaker for playing audios and a microphone for making calls, wherein the headphone further includes:

a biological feature detection module, configured to detect a biological feature of a user;

a mode switching module, configured to switch, under control of a control module, to determine whether the headphone is in a working mode supporting a biological feature detection mode;

a first communication module, configured to carry out communication between the headphone and a smart terminal;

a control module, configured to detect and determine whether an instruction is received from the smart terminal, and control, according to the instruction received from the smart terminal, the biological feature detection module, the mode switching module, the power management module and the first communication module to work, and further configured to parse the biological feature from the biological feature detection module under control of the instruction received from the smart terminal, and transmit the parsed biological feature to the smart terminal via the first communication module; and a power management module, configured to supply power to modules in the headphone.

In an optional embodiment of the embodiments of the present application, the headphone includes a connection member configured to connect the headphone to the smart terminal to implement information interaction between the headphone and the smart terminal, and the smart terminal includes a headphone jacket, the connection member mating with the headphone jacket.

In an optional embodiment of the embodiments of the present application, the connection member includes a first end configured to be electrically connected to the headphone jacket, and the mode switching module is configured to select, via switching, the connection of the first end with the microphone or connection with the first communication module, to determine whether the headphone is in the working mode supporting the biological feature detection mode.

In an optional embodiment of the embodiments of the present application, the mode switching module includes a switch array configured to select, via switching and under control of the control module, to select the connection of the first end with the microphone or connection with the first communication module, the switch array being simultaneously electrically connected to the power management module.

In an optional embodiment of the embodiments of the present application, the power management module includes a voltage conversion submodule; and when the connection member is connected to the smart terminal, the power management module is powered on by the smart terminal, and the voltage conversion submodule is configured to convert electric energy supplied by the smart terminal into power desired by the modules in the headphone to supply power to the modules.

In an optional embodiment of the embodiments of the present application, the power management module further includes a startup buffering submodule configured to buffer a power-on process, wherein the startup buffering submodule is connected between the mode switching module and the voltage conversion submodule.

In an optional embodiment of the embodiments of the present application, the power management module further includes a stabilization submodule configured to stabilize a process of supplying power to the modules in the headphone, wherein the stabilization submodule is connected between the startup buffering submodule and the switch array.

In an optional embodiment of the embodiments of the present application, the power management module further includes an energy storage submodule connected to an output terminal of the voltage conversion submodule; and when the connection member is connected to the smart terminal, the voltage conversion submodule in the power management module is configured to convert electric energy supplied by the smart terminal to charge the energy storage submodule.

In an optional embodiment of the embodiments of the present application, the connection member includes a second end configured to electrically connect the headphone jacket of the smart terminal to a left sound channel of the loudspeaker and a third end configured to electrically connect the headphone jacket of the smart terminal to a right sound channel of the loudspeaker; the first communication module is configured to receive an instruction from the smart terminal via the first end or the second end or the third end; and the first communication module is configured to transfer the parsed biological feature to the smart terminal via the first end.

In an optional embodiment of the embodiments of the present application, the biological feature detection mode includes: detecting a biological feature, parsing a detected biological feature, and transferring a parsed biological feature to a smart terminal.

In an optional embodiment of the embodiments of the present application, the biological feature detection module includes: a detection submodule configured to detect the biological feature of the user, and a signal processing submodule configured to process the detected biological feature.

In an optional embodiment of the embodiments of the present application, the detection submodule includes: a light source configured to irradiate a detected region of the user, a driver configured to drive the light source to emit light, an photoelectric converter configured to receive an optical signal reflected by the detected region and convert the optical signal into a current signal, a current-voltage converter configured to convert the current signal into a voltage signal, and an analog-to-digital converter configured to perform an analog-to-digital conversion for the voltage signal.

To better solve the above technical problem, the embodiments of the present application further provide a biological feature detection method based on a headphone, including the following steps:

S10: detecting and judging whether an instruction for performing biological feature detection is currently received from a smart terminal, if the instruction is received, performing step S20, and otherwise, continuously performing step S10;

S20: detecting and judging whether a call instruction is currently received from the smart terminal, if the call instruction is received, performing step S40, and otherwise, performing step S30;

S30: controlling a headphone to perform biological feature detection for a user, such that the headphone enters a working mode supporting a biological feature detection mode; and S40: controlling the headphone to enter a working mode supporting a call mode and returning to step S10 upon completion of the call.

To better solve the above technical problem, the embodiments of the present application provide an interaction system, including a smart terminal and a headphone configured to interact with the smart terminal. The headphone is any of the above described headphones with the biological feature detection function. The smart terminal includes a second communication module which communicates with a first communication module in the headphone and a control and processing module configured to control and process an interaction process between the smart terminal and the headphone.

The headphone with the biological feature detection function according to this embodiment of the present application switches the working mode under control of the smart terminal. Therefore, the headphone is capable of implement working mode switching under control of the smart terminal, to enable the headphone to be in the working node supporting the biological feature detection mode, so as to implement the biological feature detection function. Specifically, the power management module supplies power to the modules in the headphone, to ensure that the modules in the headphone normally work. The control module controls, according to the instruction from the smart terminal, the mode switching module to determine whether the headphone is in the working mode supporting the biological feature detection mode. Therefore, when the smart terminal issues the instruction for performing the biological feature detection, the headphone may automatically implement the biological feature detection according to the instruction from the smart terminal under control of the control module. The whole process that the headphone implements the biological feature detection function is practiced according to the instruction from the smart terminal, and during this process the user does not need to manually operate the headphone. Therefore, the biological feature detection function may be automatically implemented in the whole process, and thus the headphone has the advantages of simple and convenient operations, good user experience, wide application scope, and good practicability.

DETAILED DESCRIPTION

For better understanding of embodiments of the present application, the embodiments of the present application are thoroughly described with reference to relevant accompanying drawings. The accompanying drawings show preferred embodiments of the embodiments of the present application. However, the embodiments of the present application may be implemented in a plurality of forms or ways, and are not limited to the embodiments described herein. On the contrary, the embodiments described herein are intended to make the disclosure of the embodiments of the present application more clearly and thoroughly understood.

Unless otherwise defined, all the technical and scientific terms used in this specification convey the same meanings as the meanings commonly understood by a person skilled in the art to which the embodiments of the present application pertain. Additionally, the terms used in the specification of the embodiments of the present application are merely for describing the objective of the specific embodiments, and are not intended to limit the embodiments of the present application.

Figure 1:
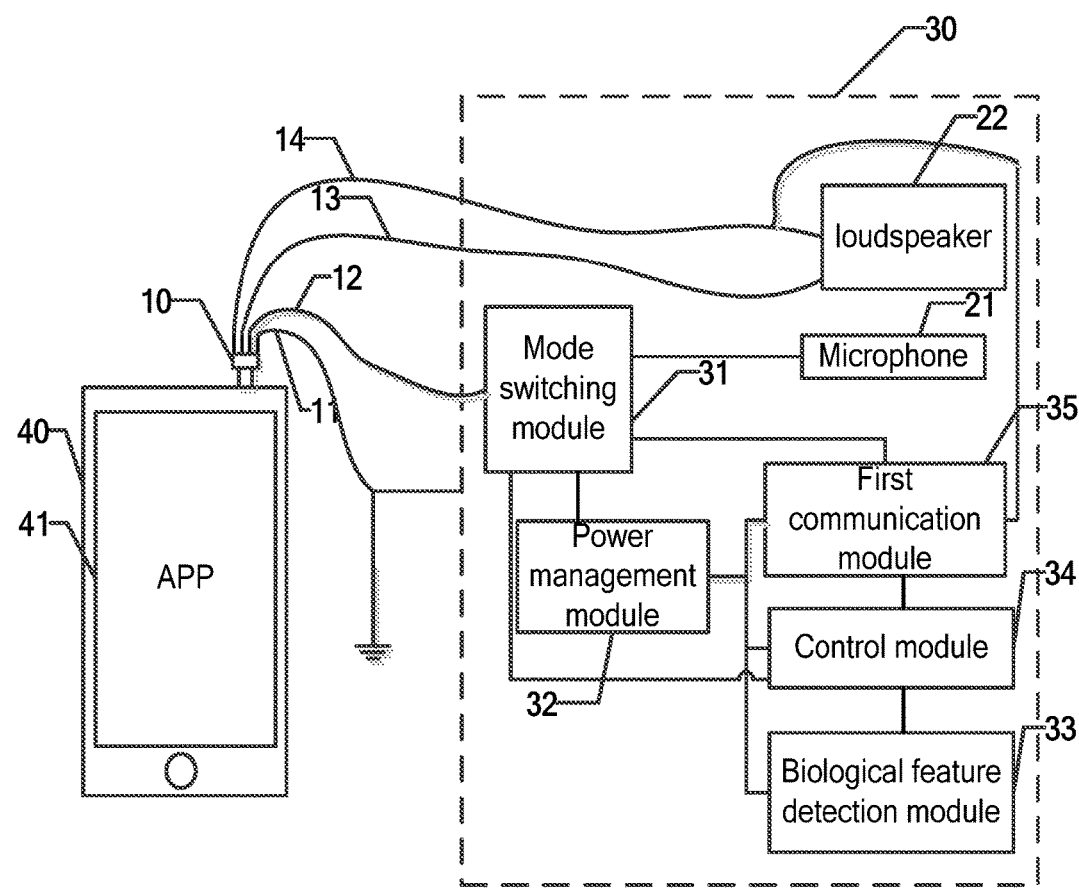
FIG. 1 is a schematic structural diagram of an interaction system formed by a wired connection between a smart terminal and a headphone according to the present application.
Figure 2:
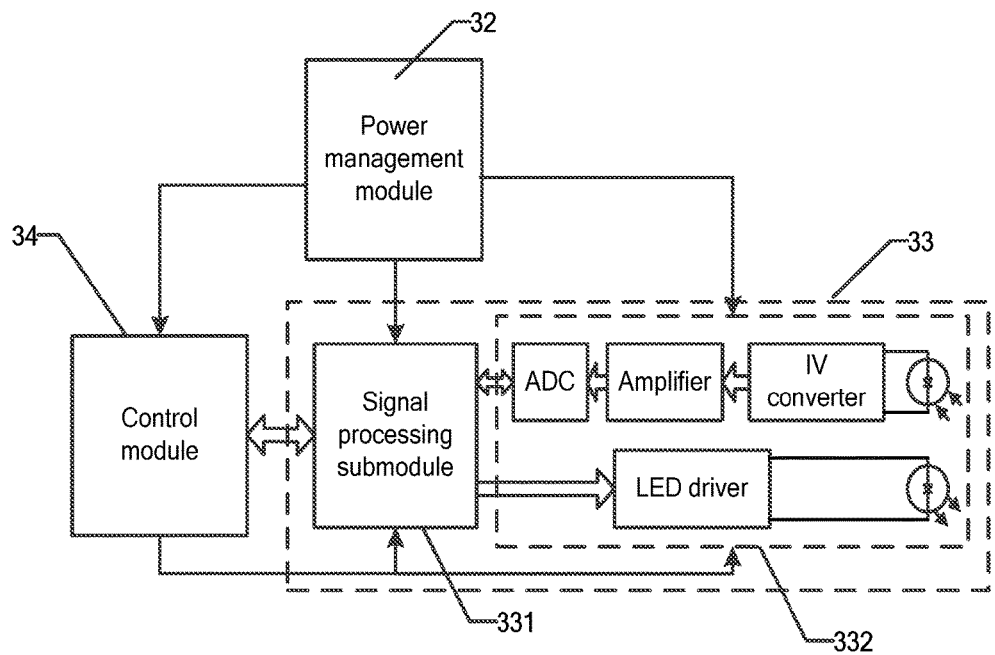
FIG. 2 is a schematic structural diagram of interactions between a power management module, a biological feature detection module and a control module according to an optional embodiment of the present application.
Figure 3:
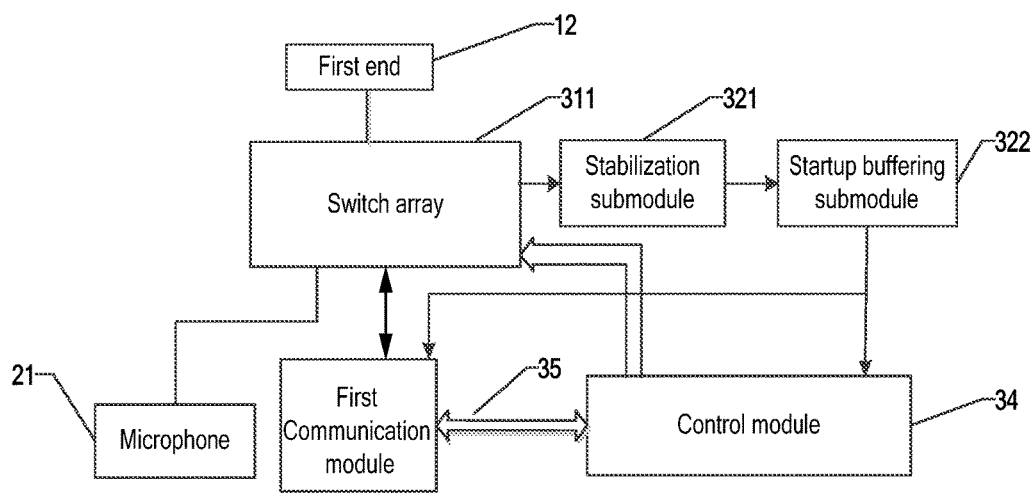
FIG. 3 is a schematic partial structural diagram of interactions between a control module, and a mode switching module, a first communication module and a power management module according to an optional embodiment of the present application.

Referring to FIG. 1 to FIG. 3, an embodiment of the present application provides a headphone 30 with a biological feature detection function, which may implement the basic audio playing function and call function of a headphone. The headphone 30 according to this embodiment of the present application mainly includes: a loudspeaker 22 (which is also referred to as a speaker) for playing audios and a microphone 21 for making calls. The headphone 30 further includes: a biological feature detection module 33, configured to detect a biological feature of a user; a mode switching module 31, configured to switching a working mode of the headphone 30 supporting or not supporting biological feature detection according to a decision by a control module that whether the headphone detects or not detects biological feature; a first communication module 35, configured to carry out communication between the headphone and a smart terminal; a control module 34, configured to detect and determine whether an instruction is received from the smart terminal, and control, according to the instruction received from the smart terminal, the biological feature detection module 33, the mode switching module 31, the power management module 32 and the first communication module 35 to work, and further configured to parse the biological feature from the biological feature detection module 33 under control of the instruction received from the smart terminal, and transmit the parsed biological feature to the smart terminal via the first communication module 35; and a power management module 32, configured to supply power to modules in the headphone 30.

The headphone 30 according to this embodiment of the present application may not be simultaneously in a call mode and a biological feature detection mode (that is, the headphone 30 may be in either the call mode or the biological feature detection mode). Therefore, the mode switching module 31 needs to switch a part of working modes of the headphone 30 under control of the control module 34. That is, the headphone 30 with the biological feature detection function according to this embodiment of the present application switches the working mode under control of the smart terminal, to enable the headphone 30 to be in the working mode supporting the biological feature detection mode, so as to implement the biological feature detection function. Specifically, the power management module 32 supplies power to the modules in the headphone 30, to ensure that the modules in the headphone 30 normally work. The control module 34 controls, according to the instruction from the smart terminal, the mode switching module 31 to determine whether the headphone 30 is in the working mode supporting the biological feature detection mode. Therefore, when the smart terminal issues the instruction for performing the biological feature detection, the headphone 30 may automatically implement the biological feature detection according to the instruction from the smart terminal under control of the control module 34. The whole process that the headphone 30 implements the biological feature detection function is practiced according to the instruction from the smart terminal, and during this process the user does not need to manually operate the headphone 30. Therefore, the biological feature detection function may be automatically implemented in the whole process, and the operations are simple and convenient. In addition, the headphone 30 according to this embodiment of the present application has a loudspeaker 22 and a microphone 21, and therefore the headphone 30 supports the audio and call function. As such, the headphone 30 may simultaneously work in a biological feature detection mode and an audio mode (or in another information interaction mode). That is, the headphone 30 may select, under control of the control module 34, whether the headphone is in the working mode supporting the biological feature detection mode. The headphone 30 according to this embodiment of the present application may implement the basic audio playing functions such as listening music, answering calls and the like, and may implement the basic call function (which may be voice calls or may be a call function with the video function) of the headphone 30 by using the microphone 21. Therefore, the headphone 30 according to this embodiment of the present application has powerful functionality, and has the advantages of convenient usage, good user experience, wide application scope and good practicability.

The control module 34 is further configured to parse the biological feature from the biological feature detection module 33 under control of the instruction from the smart terminal. The parsing may include processing the biological feature as follows: for example, filtering and denoising in the early stage, information calculation and analysis of the specific signal of the biological feature and the like (for example, filtering the noise in the signal, judging and filtering the interference caused by movement, calculating the heart beat rate based on the regular variation of the voltage, processing the heart beat data into diagram data, comparing to determine whether the user's heart beat is normal and the like, and sending such parsed data to a mobile phone via the first communication module 35 such that the data is displayed to the user via the mobile phone); the parsing may also include filtering and denoising, signal modulation, demodulation and the like operations in the early stage, such that the headphone 30 provides initial data of the biological feature of the user to the mobile phone, and the mobile phone performs operations such as calculation, analysis and the like.

The headphone 30 according to this embodiment of the present application may be in a wired structure or a wireless structure. That is, the headphone may carry out information interaction with the smart terminal (for example, a mobile phone or a Pad) in a wired manner, or may carry out information interaction with the smart terminal in a wireless manner. The specific interactive communication may be based on various communication manners in the prior art, which is not described herein any further.

In an optional embodiment of the embodiments of the present application, the headphone 30 interacts with the smart terminal in a wired manner, and has the advantages of lowering the cost and the like. The embodiments of the present application are described hereinafter with reference to the wired interaction manner. Referring to FIG. 2 and FIG. 3, the headphone 30 includes a connection member 10 configured to connect the headphone to the smart terminal to implement information interaction between the headphone 30 and the smart terminal, and the smart terminal includes a headphone jacket, the connection member 10 mating with the headphone jacket. That is, the headphone 30 implements wired communication with the smart terminal via the connection member 10. In an optional embodiment of the embodiments of the present application, the connection member 10 includes a first end 12 configured to be electrically connected to the headphone jacket, and the mode switching module 31 is configured to select, via switching, the connection of the first end 12 with the microphone or connection with the first communication module 35, to determine whether the headphone 30 is in the working mode supporting the biological feature detection mode. Referring to FIG. 1 to FIG. 6, when the first end is connected to the microphone via the mode switching module, the headphone is in the call mode, that is, the headphone may be used for making calls; and when the first end is connected to the first communication module via the mode switching module (the first end may be only electrically connected to one of the microphone and the first communication module), the headphone is in the biological feature detection mode, that is, the headphone may be also used for biological feature detection.

More optionally, the headphone 30 may be powered by the smart terminal, and when the connection member 10 is connected to the smart terminal, the power management module 32 is powered on by the smart terminal, such that power is supplied to the modules (modules/elements in the headphone which need power) in the headphone 30. Specifically, the power management module 32 includes a voltage conversion submodule configured to convert the electric energy supplied by the smart terminal into power desired by the modules in the headphone 30, such that the modules in the headphone 30 are supplied with power. As such, the headphone 30 may be compatible with more power supply manners, such that the headphone 30 may still work even if the internal power supply is exhausted. In this way, the working duration of the headphone may be prolonged, and thus the practicability thereof is extended.

In the embodiment illustrated in FIG. 2, the mode switching module 31 is simultaneously electrically connected to the first end 12, the microphone 21, the power management module 32 and the control module 34. The mode switching module 31 includes a switch array 311 controlled by the control module 34. The switch array 311 select, via switching under control of the control module, the connection of the first end 12 with the microphone 21 or connection with the first communication module 35, such that connections or disconnections between the relevant modules in the headphone 30 and the smart terminal are controlled under the instruction from the control module 34. Optionally, the microphone 21 maintains a constantly-connected state with the first end 12 of the connection member 10 by using a part of switches in the switch array, such that the microphone 21 and the smart terminal are in a constantly-connected state. As such, the initial state of the microphone is in a connected state, such that the default initial state of the headphone 30 is a state in which the headphone is compatible with the call mode. (Nevertheless, the initial state of the headphone 30 may also be made not to support the call mode by using the switch array.) The first end 12 may select, via switching, to be electrically connected to only one of the microphone 21 and the first communication module 35 by using the switch array in the mode switching module 31, such that the headphone 30 is capable of automatically controlling the switch array according to the instruction from the smart terminal under control of the control module 34 of the headphone 30, to automatically determine whether the headphone 30 enters the working mode supporting the biological feature detection mode. Therefore, no mechanical key needs to be arranged on the headphone 30, and thus the user does not need to manually operate the mechanical key. Even in such cases, the headphone 30 is capable of automatically performing the biological feature detection operation in the whole process.

In an optional embodiment, that is, in the optional embodiment where the headphone 30 is powered by the smart terminal, the switch array 311 enables the first end 12 to be simultaneously electrically connected to the power management module 32, such that the smart terminal and the power management module 32 in the headphone 30 are constantly in an electrically connected state (nevertheless, in other embodiments, the smart terminal and the power management module 32 in the headphone 30 may not be constantly in an electrically connected state). In this way, the smart terminal may constantly supply power to the headphone 30. Specifically, when the connection member 10 is connected to the smart terminal, the power management module 32 is powered on by the smart terminal, and the voltage conversion submodule (not illustrated in the drawings) included in the power management module 32 converts the electric energy supplied by the smart terminal into power desired by the modules in the headphone 30, such that power is supplied to the modules in the headphone 30.

The power management module 32 is configured to supply power to the headphone 30 and management the power supply, and specifically supply power to the first communication module 35, the control module 34 and the biological feature detection module 33. In an optional embodiment of the embodiments of the present application, the power management module 32 further includes a startup buffering submodule 322 configured to buffer a power-on process, wherein the startup buffering submodule 322 is connected between the mode switching module 31 and the voltage conversion submodule. This ensures that the headphone 30 is normally powered on in the instant when the headphone 30 is started, which prevents the headphone 30 from being repeatedly restarted during the power-on process, and ensures constant and normal working of the headphone 30. The startup buffering submodule may be arranged between the switch array and the voltage conversion submodule, which may reduce impacts caused by spike pulses and surges to the rear end during the power-on process, that is, implementing the functions of anti jitter and power-on delaying function or the like. The power management module 32 may include a stabilization submodule 321 configured to stabilize a process of supplying power to the modules in the headphone 30, wherein the stabilization submodule is connected between the startup buffering submodule and the switch array. That is, when the power supply switches to stay in another mode for a short time period and the instantaneous power consumption current is over great, the voltage of the headphone 30 is ensured to be above the normal operating voltage. For example, the stabilization submodule 321 may achieves the buffering and stabilization effect by using such an energy storage element as a capacitor. Optionally, the power management module 32 further includes an energy storage submodule (not illustrated in the drawings) connected to an output terminal of the voltage conversion submodule; and when the connection member 10 is connected to the smart terminal, the voltage conversion submodule in the power management module 32 is configured to convert electric energy supplied by the smart terminal to charge the energy storage submodule. This ensures that the headphone 30 has a backup battery, such that the headphone has more powerful functions.

Optionally, the connection member includes a first end configured to be electrically connected to the headphone jacket, and the switch array in the mode switching module selects, via switching, the connection of the first end with the microphone, the connection with the first communication module, or the connection with the power management module, to select the working mode of the headphone. That is, the first end is intermittently electrically connected to the power management module. The mode switching module selects, via switching, the connection of the first end with the microphone, the connection with the first communication module, or the connection with the power management module, to determine whether the headphone is in the working mode supporting the biological feature detection mode. That is, when the first end is connected to the microphone, the headphone is in the working mode supporting the call mode. In addition, in the biological feature detection mode, periodical switching may be carried out between the first end and the first communication module and between the first end and the power management module. When the headphone detects the biological feature of the user, within such a short time period, the first end may be temporarily disconnected from the first communication module (in this case, the first end is connected to the power management module to supply power to the biological feature detection module, that is, in the power supply mode of the headphone system), to reduce power consumption. Similarly, when data needs to be transmitted by the first communication module, the switch array may enable, under control of the control module, the first end to be only connected to the first communication module (in this case, the first end may be temporarily disconnected from the power management module, that is, in the communication mode), to upload and download of the data. In this optional manner, the power consumption of the headphone and the smart terminal may be greatly reduced.

In the embodiment illustrating the wired headphone 30, the headphone 30 is a wire-controlled headphone, and may match such a smart terminal as a mobile phone 40. At present, the headphone jacket of a mobile phone generally includes four interfaces, that is, a left sound channel, a right sound channel, a ground terminal and a microphone 21 that are configured to connect the external headphone 30. Therefore, the first end 12 of the connection member 10 in the headphone 30 according to this embodiment of the present application is configured to be connected to the microphone 21 or the first communication module 35, to carry out the biological feature detection. The connection member 10 may further optionally include: a second end 13 configured to electrically connect the headphone jacket of the smart terminal to the left sound channel of the loudspeaker 22, a third end 14 configured to electrically connect the headphone jacket of the smart terminal to the right sound channel of the loudspeaker and the ground terminal 11. The first communication module 35 is configured to receive an instruction from the smart terminal via the first end or the second end 13 or the third end 14; and the first communication module 35 is configured to transfer the parsed biological feature to the smart terminal via the first end 12. Therefore, when the headphone 30 is inserted into the smart terminal via the connection member 10, the branch where the loudspeaker 22 of the headphone 30 is configured is constantly in an electrically connected state, so as to ensure that the headphone 30 is constantly compatible with the audio mode. Therefore, when the headphone 30 is in the biological feature detection mode, the headphone 30 is practically in the working mode supporting the biological feature detection mode and the audio mode.

The headphone 30 according to this embodiment of the present application may detect various biological features, and such a detector as a sensor configured to detect the biological feature may employ any of various sensors available in the prior art, which is not described herein any further. The biological feature detection mode may include: detecting a biological feature, parsing a detected biological feature, and transferring a parsed biological feature to a smart terminal. The biological feature includes one or any combination of: heart rate, step quantity, body temperature and blood oxygen.

In an optional embodiment of the embodiments of the present application, the biological feature detection module 33 includes: a detection submodule 332 configured to detect the biological feature of the user, and a signal processing submodule 331 configured to process the detected biological feature. Optionally, the headphone 30 supports the heart rate detection function. Therefore, the detection submodule 332 includes: a light source configured to irradiate a detected region of the user, a driver (the embodiment illustrated in FIG. 2 illustrates an LED driver) configured to drive the light source to emit light, an photoelectric converter configured to receive an optical signal reflected by the detected region and convert the optical signal into a current signal, a current-voltage converter (the embodiment illustrated in FIG. 2 illustrates an IV converter) configured to convert the current signal into a voltage signal, and an analog-to-digital converter (the embodiment illustrated in FIG. 2 illustrates an ADC, and in an embodiment, an amplifier configured to amplify the signal output by the IV converter may be configured before the ADC) configured to perform an analog-to-digital conversion for the voltage signal. The detection submodule may judge a heart rate parameter of a tested object according to the regular variation of the strength of the reflected light, such that the biological feature detection module 33 supports the heart rate detection function.

In the embodiment as illustrated in FIG. 2, the biological feature detection module 33 is configured to detect a heart rate of a human body, and includes a signal processing submodule 331 and a detection submodule 332. The signal processing submodule 331 has the following functions: acquiring a heart rate detection signal from the detection submodule 332 under control of the control module 34; and processing the acquired heart rate detection signal and transferring the data to the control module 34 for processing. The processing by the detection submodule 332 includes the following operations: the LED driver drives, under control of the control module 34, the LED to irradiate a detected region; a photosensitive diode receives an optical signal reflected by the detected region and converts the optical signal into a photocurrent signal, and the photocurrent signal experiences IV conversion, signal amplification and ADC conversion, and then converted into initial data, and the initial data is transferred to the control module 34 via the signal processing submodule 331.

Therefore, the headphone according to this embodiment of the present application needs no additional power supply, and solves the power supply and communication issues of the entire system and implements the biological feature detection function by reusing the interface of the wire-controlled headphone. The headphone according to the present application does not need an external mechanical switch to manually switch between the voice call mode and the biological feature detection mode, and is capable of simultaneously implementing the biological feature detection, the audio playing and the like functions, without affecting the normal voice call function. In addition, such headphone needs no manual operations on the external mechanical switch.

Figure 4:
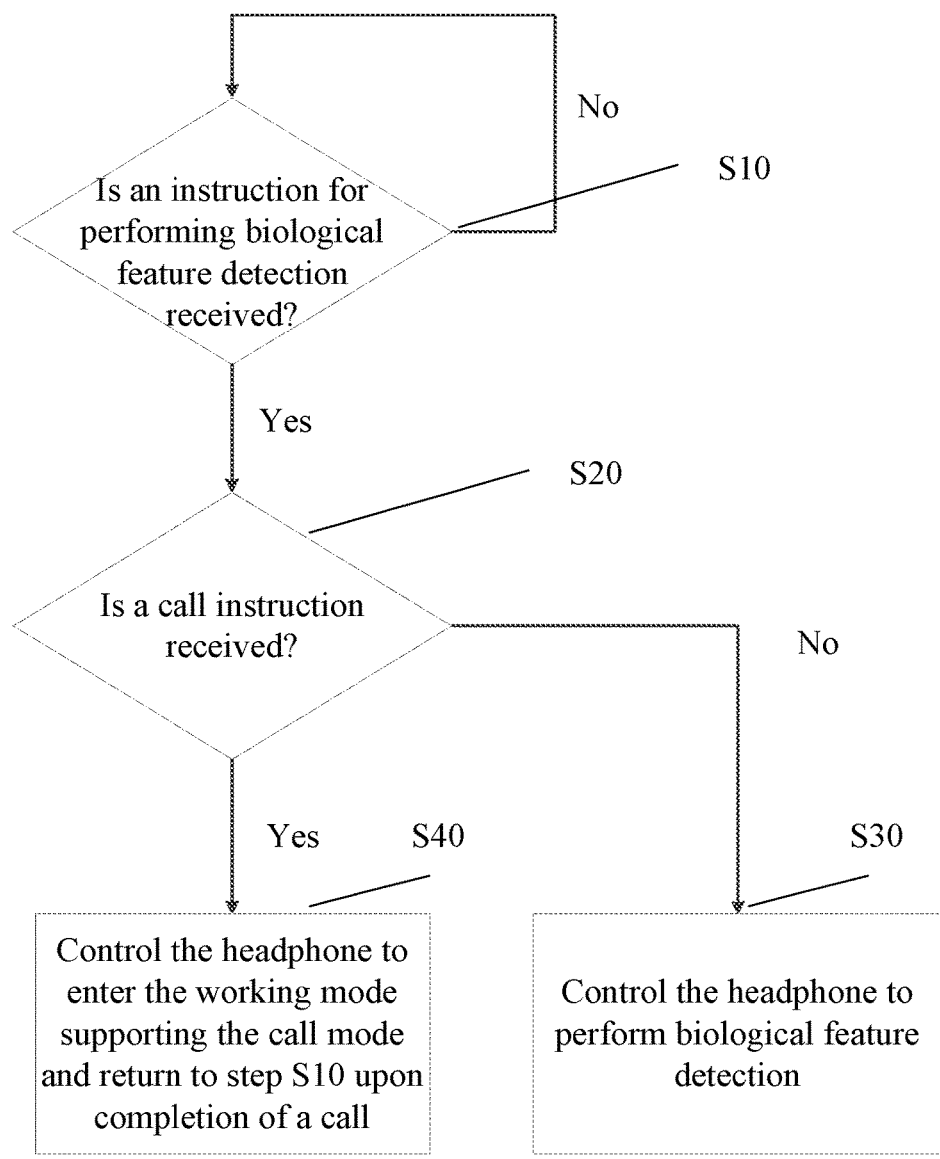
FIG. 4 is a schematic diagram of a biological feature detection method based on a headphone according to the present application.
Figure 5:
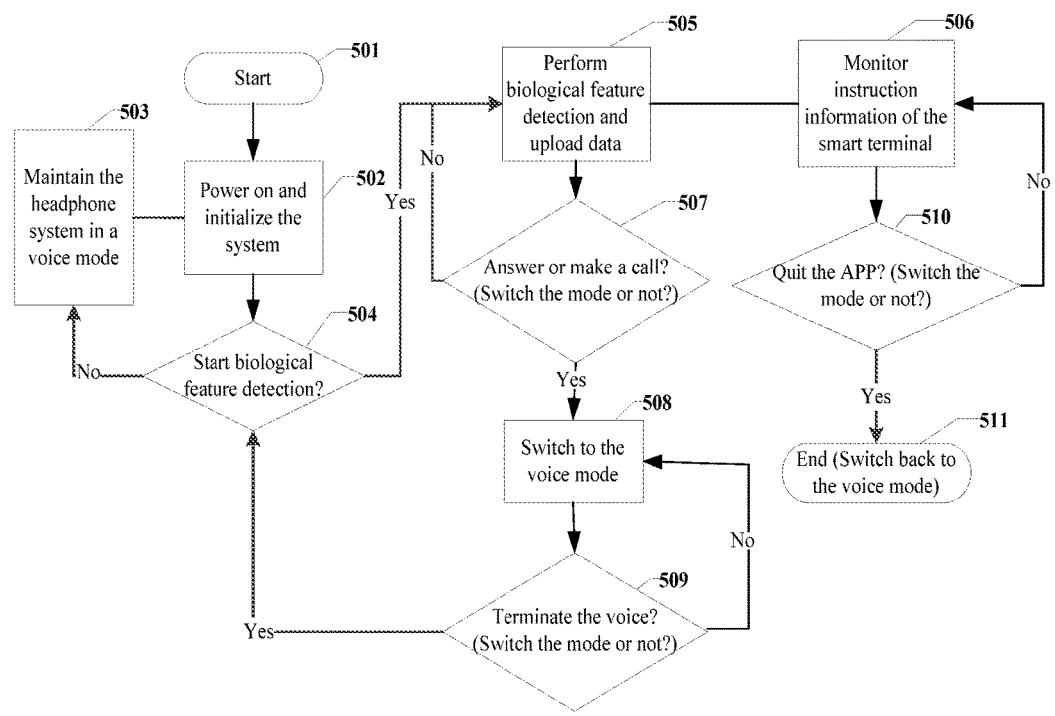
FIG. 5 is a schematic diagram of a biological feature detection method based on a headphone according to an optional embodiment of the present application.
Figure 6:
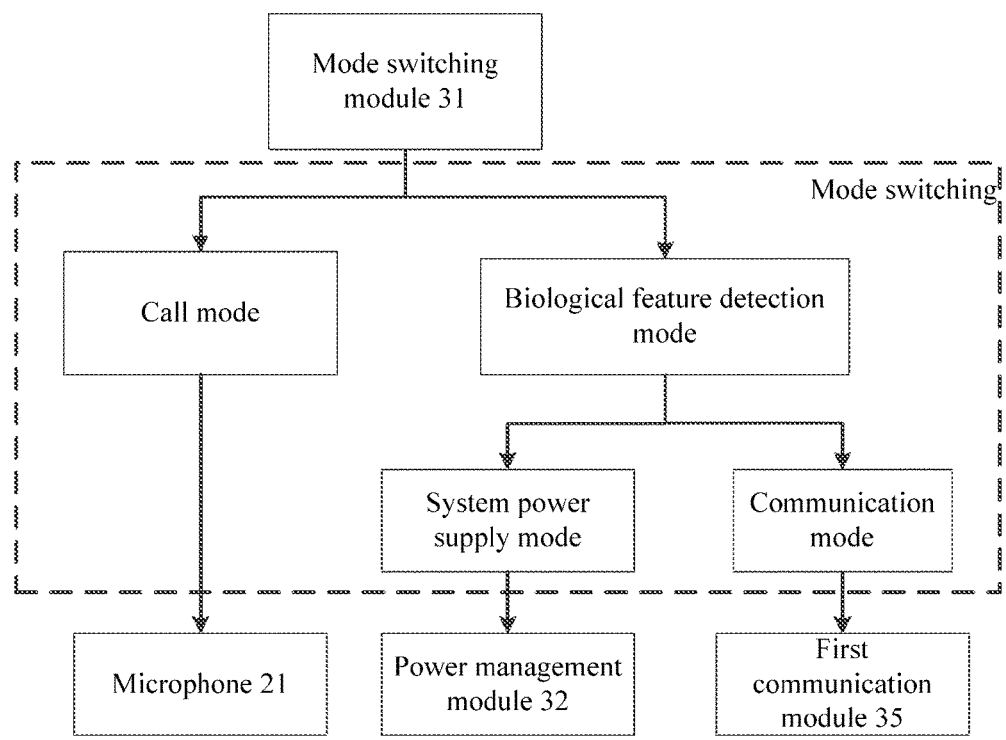
FIG. 6 is a schematic diagram of mode switching by a mode switching module according to an optional embodiment of the present application.

Referring to FIG. 4 and FIG. 5, an embodiment of the present application further provides a biological feature detection method based on a headphone, including the following steps:

S10: detecting and judging whether an instruction for performing biological feature detection is currently received from a smart terminal, if the instruction is received, performing step S20, and otherwise, continuously performing step S10;

S20: detecting and judging whether a call instruction is currently received from the smart terminal, if the call instruction is received, performing step S40, and otherwise, performing step S30;

S30: controlling a headphone to perform biological feature detection for a user, such that the headphone enters a working mode supporting a biological feature detection mode; and S40: controlling the headphone to enter a working mode supporting a call mode and returning to step S10 upon completion of the call.

The biological feature detection mode includes: detecting a biological feature, parsing a detected biological feature, and transferring a parsed biological feature to a smart terminal. Therefore, in step S10, it is detected whether a user issues an instruction for detecting the biological feature via the smart terminal. If a user issues such an instruction, it is judged whether an instruction for making a call is received. That is, when the headphone fails to simultaneously implement the call and the biological feature detection, the priority of the call instruction of the headphone is higher than that of the instruction for detecting the biological feature, to ensure the basic call function of the headphone. When the instruction for detecting the biological feature is received and no call instruction is received, the headphone is controlled to enter the biological feature detection mode. In addition, in this case, the headphone may simultaneously support the biological feature detection mode and other modes (for example, the audio mode). Therefore, when the headphone starts to enter the biological feature detection mode, it signifies that the headphone enters the working mode supporting the biological feature detection mode.

Since the headphone generally needs to constantly support the audio playing function, the headphone needs to be constantly in a mode supporting audio playing. Therefore, when the headphone starts to enter the biological feature detection mode, it signifies that the headphone enters the working mode supporting the biological feature detection mode.

In an optional embodiment of the embodiments of the present application, the method further includes: in the process of performing step S30, simultaneously detecting and judging whether an instruction for stopping a biological feature detection is currently received from the smart terminal and whether a call instruction is currently received from the smart terminal, if the instruction for stopping a biological feature detection is currently received from the smart terminal, controlling the headphone to exit biological feature detection mode, and if the call instruction is received from the smart terminal, performing step S40. Therefore, the priority of the call instruction of the headphone is always higher than that of the instruction for detecting the biological feature of the headphone, to ensure the basic call function of the headphone. The headphone may simultaneously implement such functions as biological feature detection, audio playing and the like. Therefore, the basic voice call function is not affected, and no external mechanical switch and thus no manual operations are needed.

Hereinafter the process of performing the biological feature detection by using the headphone according to the embodiments of the present application is described with reference to an optional embodiment. As illustrated in FIG. 5, the initial state of the headphone is defaulted to be in the call mode, and the headphone automatically switches to the call mode before the biological feature detection is performed, such that the headphone is constantly preferentially in the call mode (that is, in a call standby state for making calls when necessary).

Step 501: The process starts, and the headphone is inserted into the smart terminal.

Step 502: The entire headphone system is powered on; and the headphone system initializes settings of a relevant register, for example, the timer, IO status and the like, and the power management module is charged.

Step 503: The headphone system is defaulted to be in a voice mode, that is, the initial state of the first end 12 is connected to the microphone.

Step 504: It is judged whether an APP of the smart terminal sends a start signal indicative of starting the biological feature detection; if no start signal is received, the voice mode is maintained; and if such a start signal is received, step 505 is performed.

Step 505: The headphone starts the biological feature detection, and transfers the acquired biological feature signal to the smart terminal.

Step 506: While step 505 is performed, instruction information sent by the smart terminal is constantly monitored.

Step 507: It is judged whether a call signal for starting a voice call is received; if no such call signal is received, the biological feature detection is continuously performed.

Step 508: If such a call signal is received, the biological feature detection is quickly interrupted, and the headphone switches to a voice call mode.

Step 509: It is judged whether the voice call is terminated; and if the voice call is terminated, it is continuously judged whether to starts the biological feature detection.

Step 510: While step 506 is performed, it is judged whether the smart terminal proactively stops the biological feature detection.

Step 511: If the smart terminal proactively stops the biological feature detection, the headphone automatically switches to the voice mode; and otherwise, step 506 is continuously performed.

Optionally, the headphone selects, via the mode switching module, connection or disconnection between the first end and the first communication module of the headphone, so as to determine whether the headphone enters the working mode supporting the biological feature detection mode. That is, the working mode may be a mode simultaneously supporting a biological identification mode, an audio mode and other possible modes. The first end of the headphone and the microphone of the headphone are constantly in a connected state, such that the call function whose use frequency is generally higher than the use frequency of the biological feature detection function may be more quickly and better implemented. When the connection member of the headphone is connected to the smart terminal, the headphone is powered on by the smart terminal and the smart terminal supplies power to the headphone. The power management module of the headphone further buffers the power-on process and/or stabilizes the power supply process.

An embodiment of the present application further provides an interaction system, including a smart terminal 40 and a headphone 30 configured to interact with the smart terminal. The headphone is any of the above described headphones with the biological feature detection function. The smart terminal includes a second communication module (not illustrated in the drawings) which communicates with a first communication module in the headphone and a control and processing module 41 (that is, an APP) configured to control and process an interaction process between the smart terminal and the headphone. Such operations as calculation and analysis of the detection signal obtained by the biological feature detection module may be practiced in the control module of the headphone, or may be practiced in such a smart terminal as a mobile phone.

In conclusion, the headphone according to the embodiments of the present application has the following advantages:

1. The headphone is capable of automatically implementing the biological feature detection function in the whole process, and the headphone supports the voice call, audio playing, biological detection and the like functions.

2. In the implementation of the biological feature detection function, no additional power supply is needed, and the power supply and communication issues of the entire system are solved by reusing the interface of the wire-controlled headphone. In addition, the microphone interface is capable of both receiving signals and sending signals. That is, the issue of power supply to the headphone may be solved, the communication issue of the headphone may be solved, the issue of extracting the biological feature may be solved, and the issue of mode switching of the headphone may be solved. Limited interface resources are fully utilized, more functions are implemented without affecting the existing functions, and the usage is more convenient.

3. The headphone may simultaneously implement such functions as biological feature detection, audio playing and the like. Therefore, the basic voice call function is not affected, and no external mechanical switch and thus no manual operations are needed.

The algorithms and displays provided herein are not inherently related to any specific computer, virtual system or other device. Various general-purpose systems may also be used with the teachings herein. According to the above description, the structure required for constructing such systems is obvious. In addition, the present application is not directed to any specific programming language. It should be understood that the content of the present application described herein may be carried out utilizing various programming languages, and that the above description for a specific language is for the sake of disclosing preferred embodiments of the present application.

In the specification provided herein, a plenty of particular details are described. However, it can be appreciated that an embodiment of the present application may also be practiced without these particular details. In some embodiments, well known methods, structures and technologies are not illustrated in detail so as not to obscure the understanding of the specification.

Likewise, it shall be understood that, to streamline the present application and facilitate understanding of one or more of various aspects of the present application, in the above description of the exemplary embodiments of the present application, various features of the present application are sometimes incorporated in an individual embodiment, drawing or description thereof. However, the method according to the present application shall not be explained to embody the following intension: the present application seeking protection claims more features than those explicitly disclosed in each of the appended claims. To be more exact, as embodied in the appended claims, the inventive aspects lie in that fewer features than all the features embodied in an individual embodiment as described above. Therefore, the claims observing the specific embodiments are herein incorporated into the specific embodiments, and each claim may be deemed as an individual embodiment of the present application.

Those skilled in the art should understand that modules in the devices according to the embodiments may be adaptively modified and these modules may be configured in one or more devices different from the embodiments herein. Modules or units or components in the embodiments may be combined into a single module or unit or component, and additionally these modules, units or components may be practiced in a plurality of submodules, subunits or subcomponents. Besides that such features and/or processes or at least some of the units are mutually exclusive, all the features disclosed in this specification (including the appended claims, abstract and accompanying drawings) and all the processes or units in such disclosed methods or devices may be combined in any way. Unless otherwise stated, each of the features disclosed in this specification (including the appended claims, abstract and accompanying drawings) may be replaced by a provided same, equivalent or similar substitution.

In addition, those skilled in the art shall understand that, although some embodiments described herein include some features included in other embodiments, rather than other features, a combination of the features in different embodiments signifies that the features are within the scope of the present application and different embodiments may be derived. For example, in the claims appended hereinafter, any one of the embodiments seeking protection may be practiced in any combination manner.

Reference herein to "one embodiment", "an embodiment" or to "one or more embodiments" implies that a particular feature, structure, or characteristic described in connection with the embodiments is included in at least one embodiment of the present application. Further, it should be noted that instances of the phrase "in one embodiment" herein are not necessarily all referring to the same embodiment.

In the specification provided herein, a plenty of particular details are described. However, it can be appreciated that an embodiment of the present application may also be practiced without these particular details. In some embodiments, well known methods, structures and technologies are not illustrated in detail so as not to obscure the understanding of the specification.

It should be noted that the above embodiments illustrate rather than limit the present application, and those skilled in the art may design alternative embodiments without departing from the scope of the appended claims. In the claims, any reference sign placed between the parentheses shall not be construed as a limitation to a claim. The word "comprise" does not exclude the presence of an element or a step not listed in a claim. The word "a" or "an" preceding an element does not exclude the presence of a plurality of such elements. The present application may be implemented by means of a hardware comprising several distinct elements and by means of a suitably programmed computer. In a unit claim enumerating several devices, several of the devices may be embodied by one and the same hardware item. Use of the words "first", "second", "third" and the like does not mean any ordering. Such words may be construed as naming.

The invention claimed is:

1. A headphone with a biological feature detection function, comprising a loudspeaker for playing audio and a microphone for making calls, wherein the headphone further comprises:
   a biological feature detection module, configured to detect a biological feature of a user;
   a mode switching module, configured to switching a working mode of the headphone supporting or not supporting biological feature detection according to a decision by a control module that whether the headphone detects or not detects the biological feature;
   a first communication module, configured to carry out communication between the headphone and a smart terminal;
   the control module, configured to detect and determine whether an instruction is received from the smart terminal, and control, according to the instruction received from the smart terminal, the biological feature detection module, the mode switching module, a power management module and the first communication module to work, and further configured to parse the biological feature from the biological feature detection module under control of the instruction received from the smart terminal, and transmit the parsed biological feature to the smart terminal via the first communication module;
   the power management module, configured to supply power to modules in the headphone; and
   a connection member configured to connect the headphone to the smart terminal to implement information interaction between the headphone and the smart terminal, and the smart terminal comprises a headphone jacket, the connection member mating with the headphone jacket,
      wherein the connection member comprises a first end configured to be electrically connected to the headphone jacket, and the mode switching module is configured to select, via switching, the connection of the first end with the microphone or connection with the first communication module, to determine whether the headphone is in the working mode supporting the biological feature detection mode.

2. The headphone according to claim 1, wherein the mode switching module comprises a switch array configured to select, via switching and under control of the control module, the connection of the first end with the microphone or connection with the first communication module, the switch array being simultaneously electrically connected to the power management module.

3. The headphone according to claim 1, wherein the mode switching module is configured to select, via switching, the connection of the first end with the microphone, the connection with the first communication module, or the connection with the power management module, to determine whether the headphone is in the working mode supporting the biological feature detection mode.

4. The headphone according to claim 3, wherein the mode switching module comprises a switch array configured to select, via switching, the connection of the first end with the microphone, the connection with the first communication module, or the connection with the power management module; wherein in a power-on or biological feature detection mode, the switch array is electrically connected to the power management module and periodically switches to be connected to the first communication module to transmit the biological feature, and upon entry into a working mode supporting a call mode, the switch array is connected to the microphone.

5. The headphone according to claim 1, wherein the connection member comprises a second end configured to electrically connect the headphone jacket of the smart terminal to a left sound channel of the loudspeaker and a third end configured to electrically connect the headphone jacket of the smart terminal to a right sound channel of the loudspeaker; the first communication module is configured to receive an instruction from the smart terminal via the first end or the second end or the third end; and the first communication module is configured to transfer the parsed biological feature to the smart terminal via the first end.

6. The headphone according to claim 1, wherein the biological feature detection module comprises: a detection submodule configured to detect the biological feature of the user, and a signal processing submodule configured to process the detected biological feature;
   wherein the detection submodule comprises:
      a light source configured to irradiate a detected region of the user, a driver configured to drive the light source to emit light, a photoelectric converter configured to receive an optical signal reflected by the detected region and convert the optical signal into a current signal, a current-voltage converter configured to convert the current signal into a voltage signal, and an analog-to-digital converter configured to perform an analog-to-digital conversion for the voltage signal.

7. The headphone according to claim 1, wherein the power management module comprises a voltage conversion submodule; if the connection member is connected to the smart terminal, the power management module is powered on by the smart terminal, and the voltage conversion submodule is configured to convert electric energy supplied by the smart terminal into power desired by the modules in the headphone to supply power to the modules.

8. The headphone according to claim 7, wherein the power management module further comprises a startup buffering submodule configured to buffer a power-on process, wherein the startup buffering submodule is connected between the mode switching module and the voltage conversion submodule.

9. The headphone according to claim 8, wherein the power management module further comprises a stabilization submodule configured to stabilize a process of supplying power to the modules in the headphone upon completion of power-on, wherein the stabilization submodule is connected between the startup buffering submodule and the switch array.

10. The headphone according to claim 7, wherein the power management module further comprises an energy storage submodule connected to an output terminal of the voltage conversion submodule; and when the connection member is connected to the smart terminal, the voltage conversion submodule is configured to convert electric energy supplied by the smart terminal to charge the energy storage submodule.

11. A biological feature detection method executed by a headphone, wherein the headphone comprises a biological feature detection module configured to detect a biological feature of a user; a mode switching module configured to switching a working mode of the headphone supporting or not supporting biological feature detection according to a decision by a control module that whether the headphone detects or not detects the biological feature; a first communication module configured to carry out communication between the headphone and a smart terminal; the control module configured to detect and determine whether an instruction is received from the smart terminal, and control, according to the instruction received from the smart terminal, the biological feature detection module, the mode switching module, a power management module and the first communication module to work, and further configured to parse the biological feature from the biological feature detection module under control of the instruction received from the smart terminal, and transmit the parsed biological feature to the smart terminal via the first communication module; and the power management module configured to supply power to modules in the headphone, the biological feature detection method comprising:

S10: detecting and judging with the control module whether an instruction for performing biological feature detection is currently received from the smart terminal via the first communication module, if the instruction is received, performing step S20, and otherwise, continuously performing step S10;

S20: detecting and judging with the control module whether a call instruction is currently received from the smart terminal via the first communication module, if the call instruction is received, performing step S40, and otherwise, performing step S30;

S30: controlling with the control module the headphone to perform biological feature detection for a user, such that the headphone enters with the mode switching module a working mode supporting a biological feature detection mode implemented by the biological feature detection module; and S40: controlling with the control module the headphone to enter with the mode switching module a working mode supporting a call mode and returning to step S10 upon completion of the call.

12. The method according to claim 11, further comprising: in the process of performing step S30, simultaneously detecting and judging with the control module whether an instruction for stopping a biological feature detection is currently received from the smart terminal and whether a call instruction is currently received from the smart terminal via the first communication module, if the instruction for stopping a biological feature detection is currently received from the smart terminal via the first communication module, controlling with the control module the headphone to exit biological feature detection mode, and if the call instruction is received from the smart terminal via the first communication module, performing step S40.

13. The method according to claim 11, wherein the instruction is received from the smart terminal via a connection member connected configured to connect the headphone to the smart terminal to implement information interaction between the headphone and the smart terminal, and the smart terminal comprises a headphone jacket, the connection member mating with the headphone jacket.

14. The method according to claim 13, wherein when the connection member of the headphone is electrically connected to the smart terminal, the headphone is powered on via the smart terminal and the smart terminal supplies power to the headphone.

15. The method according to claim 13, wherein when the connection member of the headphone is electrically connected to the smart terminal, the headphone is powered on via the smart terminal and the smart terminal charges an energy storage module in the headphone.

16. The method according to claim 13, wherein the connection member of the headphone comprises a second end configured to electrically connect the headphone jacket of the smart terminal to a left sound channel of the loudspeaker and a third end configured to electrically connect the headphone jacket of the smart terminal to a right sound channel of the loudspeaker; the first communication module of the headphone is configured to receive an instruction from the smart terminal via the first end or the second end or the third end; and the first communication module is configured to transfer the parsed biological feature to the smart terminal via the first end.

17. An interaction system, comprising a smart terminal and a headphone interacting with the smart terminal, wherein the headphone comprises:

a biological feature detection module, configured to detect a biological feature of a user;

a mode switching module, configured to switch, under control of a control module, to determine whether the headphone performs biological feature detection, such that whether the headphone is in a working mode supporting a biological feature detection mode is determined;

a first communication module, configured to carry out communication between the headphone and a smart terminal;

the control module, configured to detect and determine whether an instruction is received from the smart terminal, and control, according to the instruction received from the smart terminal, the biological feature detection module, the mode switching module, a power management module and the first communication module to work, and further configured to parse, under control of the instruction received from the smart terminal, the biological feature from the biological feature detection module, and transmit the parsed biological feature to the smart terminal via the first communication module;

the power management module, configured to supply power to modules in the headphone; and a connection member configured to connect the headphone to the smart terminal to implement information interaction between the headphone and the smart terminal, and the smart terminal comprises a headphone jacket, the connection member mating with the headphone jacket, the connection member comprises a first end configured to be electrically connected to the headphone jacket, and the mode switching module is configured to select, via switching, the connection of the first end with the microphone or connection with the first communication module, to determine whether the headphone is in the working mode supporting the biological feature detection mode, and the smart terminal comprises:
- a second communication module configured to communicate with the first communication module in the headphones; and
- a control and processing module configured to control and process an interaction process between the smart terminal and the headphone.

18. The headphone according to claim 3, wherein the first end of the headphone and the microphone of the headphone are in a normally-connected state.

19. The headphone according to claim 1, wherein the power management module of the headphone is configured to further buffer a power-on process of the headphone and/or stabilize a power supply process of the headphone.

* * * * *